United States Patent
Uto et al.

(10) Patent No.: US 10,322,147 B2
(45) Date of Patent: Jun. 18, 2019

(54) ENZYME-TREATED BOVINE COLOSTRUM, PREPARATION METHOD THEREOF, COMPOSITION, AND FOODS AND BEVERAGES

(71) Applicant: SAISEI PHARMA CO., LTD., Moriguchi-shi, Osaka (JP)

(72) Inventors: Yoshihiro Uto, Tokushima (JP); Hitoshi Hori, Tokushima (JP); Toshio Inui, Moriguchi (JP); Kentaro Kubo, Moriguchi (JP)

(73) Assignee: SAISEI PHARMA CO., LTD., Moriguchi-Shi (JP)

( * ) Notice: Subject to any disclaimer, the term of this patent is extended or adjusted under 35 U.S.C. 154(b) by 392 days.

(21) Appl. No.: 15/100,505

(22) PCT Filed: Dec. 11, 2014

(86) PCT No.: PCT/JP2014/082888
§ 371 (c)(1),
(2) Date: May 31, 2016

(87) PCT Pub. No.: WO2015/087981
PCT Pub. Date: Jun. 18, 2015

(65) Prior Publication Data
US 2016/0296566 A1    Oct. 13, 2016

(30) Foreign Application Priority Data
Dec. 13, 2013   (JP) ................. 2013-257888

(51) Int. Cl.
| | | |
|---|---|---|
| A61K 35/20 | (2006.01) | |
| A23C 9/12 | (2006.01) | |
| A23C 9/20 | (2006.01) | |
| A23L 2/66 | (2006.01) | |
| A23L 33/19 | (2016.01) | |

(52) U.S. Cl.
CPC ............ *A61K 35/20* (2013.01); *A23C 9/1206* (2013.01); *A23C 9/206* (2013.01); *A23L 2/66* (2013.01); *A23L 33/19* (2016.08); *A23V 2002/00* (2013.01)

(58) Field of Classification Search
CPC .................................................... A61K 35/20
See application file for complete search history.

(56) References Cited

U.S. PATENT DOCUMENTS

| | | | |
|---|---|---|---|
| 6,426,109 B1 * | 7/2002 | Ehsani ................. | A23C 9/1422 426/478 |
| 2013/0243880 A1 | 9/2013 | Uto et al. | |
| 2014/0213522 A1 | 7/2014 | Uto et al. | |
| 2015/0152163 A1 | 6/2015 | Uto et al. | |

FOREIGN PATENT DOCUMENTS

| | | |
|---|---|---|
| EP | 2 612 921 A1 | 7/2013 |
| JP | 5-97695 A | 4/1993 |
| JP | 6-99314 B2 | 12/1994 |
| JP | 2005-508892 A | 4/2005 |
| WO | WO 03/016348 A2 | 2/2003 |
| WO | WO 2012/029954 A1 | 3/2012 |
| WO | WO 2013/038997 A1 | 3/2013 |

OTHER PUBLICATIONS

Definition of beta-galactosidase from Wikipedia, pp. 1-4, accessed on Aug. 19, 2018 (Year: 2018).*
International Preliminary Report on Patentability and Written Opinion of the International Searching Authority (Forms PCT/IB/338, PCT/IB/373 and PCT/ISA/237) dated Jun. 23, 2016, for International Application No. PCT/JP2014/082888.
Fukuda, "Transport proteins in milk", Heisei 25 Nendo Rakuno Kagaku Simposium Koen Yoshi, Milk Science, Aug. 8, 2013, vol. 62, No. 2, pp. 41 to 42, p. 41, right column, 4th paragraph.
International Search Report, issued in PCT/JP2014/082888, dated Mar. 10, 2015.
Okamura et al., "Hito Kessei Gc protein Subtype no Tosa Kozo Kaiseki", Abstracts of Annual Meeting of Pharmaceutical Society of Japan, Mar. 6, 2006, vol. 126, No. 3, p. 51, P28[R]am-114.

* cited by examiner

*Primary Examiner* — Qiuwen Mi
(74) *Attorney, Agent, or Firm* — Birch, Stewart, Kolasch & Birch, LLP

(57) ABSTRACT

An object of the present invention is to provide a method of preparing an enzyme-treated bovine colostrum, comprising a step of bringing a bovine colostrum into contact with β-galactosidase, and a pharmaceutical composition comprising the enzyme-treated bovine colostrum. The enzyme-treated bovine colostrum is useful for treatment, prevention, amelioration and maintenance of remission of diseases such as a cancer and an infectious disease.

16 Claims, 2 Drawing Sheets

ENZYME-TREATED BOVINE COLOSTRUM, PREPARATION METHOD THEREOF, COMPOSITION, AND FOODS AND BEVERAGES

TECHNICAL FIELD

The present invention relates to a pharmaceutical composition comprising an enzyme-treated bovine colostrum which is useful for treatment and prevention of diseases such as a cancer and an infectious disease, and to a method of preparing the same.

BACKGROUND ART

Macrophage has a function of treating waste products in a human body and a defensive function against pathogens such as a microbe and a virus, and tumor cells. Macrophage also has a function as an effector of cell immunity via presentation of an antigen to T cell and production of interleukin 1. Accordingly, it is important to activate macrophage for treatment and prevention of a cancer and an infectious disease, and the activation of macrophage makes it possible to carry out treatment and prevention of a cancer and an infectious disease.

A factor for activating macrophage is, for example, an interferon, and its clinical application has been carried out. In addition, it is known that a certain kind of polysaccharides has an immunostimulating activity, and some of them are expected to be developed as an antiviral agent and an anticancer agent (Patent Document 1 or 2).

Patent Document 3 describes that a human blood serum treated with an enzyme (β-galactosidase or β-galactosidase and sialidase) has an activity of macrophage activation.

PRIOR ART DOCUMENT

Patent Document

Patent Document 1: JP H05-097695 A
Patent Document 2: JP H06-099314 B
Patent Document 3: WO 2013/038997

SUMMARY OF THE INVENTION

Problem to be Solved by the Invention

An object of the present invention is to provide an enzyme-treated bovine colostrum which is useful for treatment, prevention, amelioration and maintenance of remission of diseases such as a cancer and an infectious disease, a method of preparing the same, and a composition and various products comprising the same.

Means to Solve the Problem

The present inventors have made intensive studies and as a result, have found that when a bovine colostrum is subjected to enzyme treatment by bringing the bovine colostrum into contact with a specific enzyme, that is β-galactosidase or β-galactosidase and sialidase, the treated bovine colostrum shows excellent macrophage activating action. The present inventors have made further studies and have completed the present invention.

Namely, the present invention relates to:

[1] a method of preparing an enzyme-treated bovine colostrum comprising a step of bringing a bovine colostrum into contact with β-galactosidase,

[2] the preparation method according to the above [1], further comprising a step of bringing the bovine colostrum into contact with sialidase,

[3] an enzyme-treated bovine colostrum prepared by the preparation method according to the above [1] or [2],

[4] the enzyme-treated bovine colostrum according to the above [3], comprising proteins in an amount of from 0.02 μg to 40 mg, preferably 0.02 μg to 20 mg, more preferably 0.2 μg to 20 mg, more preferably 2 μg to 20 mg, more preferably 20 μg to 20 mg, more preferably 200 μg to 10 mg, more preferably 200 μg to 2 mg for one dose,

[5] the pharmaceutical composition comprising the enzyme-treated bovine colostrum according to the above [3] or [4],

[6] the pharmaceutical composition according to the above [5], wherein the pharmaceutical composition is used for a cancer or an infectious disease,

[7] a composition for food or beverage, comprising the enzyme-treated bovine colostrum according to the above [3] or [4],

[8] a food or beverage comprising the composition for food or beverage according to the above [7].

Effects of the Invention

The enzyme-treated bovine colostrum of the present invention has an excellent macrophage activating action, particularly intestinal macrophage activating action, and therefore, is useful for treatment and prevention of a cancer and an infectious disease, and can be used as an anticancer agent, an anti-infectious agent and the like.

Further, use of the enzyme-treated bovine colostrum makes it possible to provide a quasi drug, a composition for food or beverage and a food or beverage which are useful for prevention, amelioration and maintenance of remission of the above-mentioned diseases.

Furthermore, the enzyme-treated bovine colostrum according to the present invention has advantages such as easy preparation and low cost since it can be prepared by treating a bovine colostrum with β-galactosidase or β-galactosidase and sialidase.

EMBODIMENT FOR CARRYING OUT THE INVENTION

<Bovine Colostrum>

Figure 1:
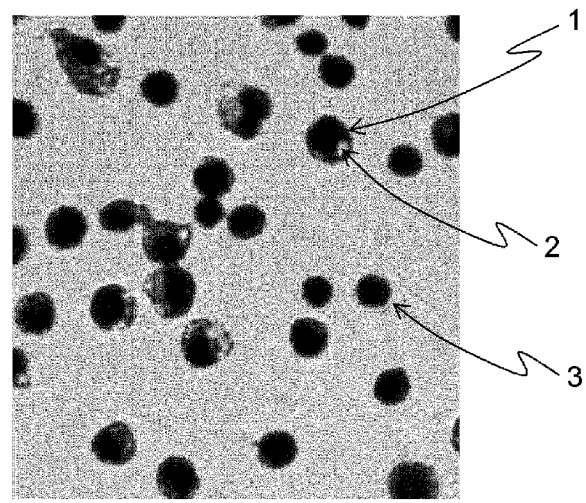
FIG. 1 is a photograph used in place of a drawing, which shows the state of macrophages subjected to Giemsa-staining.

The bovine colostrum to be used in the present invention means milk secreted by a mother cow by the 10th day after delivery of a calf, preferably milk secreted by the 7th day, more preferably by the 5th day. In the present invention, any kind of bovine colostrums can be used irrespective of kinds of cows such as Holstein and Japanese Black.

<Enzyme>

β-galactosidase to be used in the present invention is not limited particularly, and any kind of known β-galactosidases can be used. Examples are one derived from *Escherichia coli*, one derived from bovine liver, and the like. Examples of commercially available β-galactosidases are Catalogue No. 072-04141 of Wako Pure Chemical Industries, Ltd., G1875 of SIGMA-ALDRICH, and the like.

In the present invention, β-galactosidases can be used alone or can be used in combination of two or more thereof.

Sialidase to be used in the present invention is not limited particularly, and any kind of known sialidases can be used. Examples are one derived from *Clostridium perfringens*, one derived from *Streptococcus* 6646K, one derived from *Vibrio cholerae*, one derived from *Arthrobacter ureafaciens*, and the like. Examples of commercially available sialidases are Sigma product Nos. N2876, N2133, N2904, N3001 and N5631 of SIGMA-ALDRICH, Code No. 120052 of SEIKA-GAKU BIOBUSINESS CORPORATION, Catalogue # P0720L and P0720S of BioLabs, and the like.

In the present invention, sialidases can be used alone or can be used in combination of two or more thereof.

<Treatment with Enzyme>

In the present invention, it is preferable that the bovine colostrum is brought into contact with β-galactosidase or sialidase (enzyme treatment) by using a sufficient amount of enzyme for a sufficient period of time to such an extent that the enzyme reaction does not proceed substantially any more. For such a purpose, though an amount and time for the treatment depend on kind of an enzyme, for example, when Catalogue No. 072-04141 of Wako Pure Chemical Industries, Ltd. is used as β-galactosidase, it is enough to use the enzyme in an amount of 65 mU to 100 μl of a bovine colostrum. Further, for example, when the product No. N2876 of SIGMA-ALDRICH is used as sialidase, it is enough to use the enzyme in an amount of 65 mU to 100 μl of a bovine colostrum. In this case, it is sufficient to carry out the enzyme treatment for three hours.

The enzyme treatment can be carried out in a vessel of free choice by adding these enzymes into a bovine colostrum, and if desired, a buffering solution usually used in this field may be added thereto in order to adjust a total protein concentration in the bovine colostrum. Examples of such a buffering solution are saline solution, phosphate buffered saline (SPB), Ringer solution, and the like.

The enzyme treatment temperature is not limited particularly as far as the enzyme exhibits its activity, and is a temperature around 37° C. where the enzyme usually shows a high activity.

The enzyme treatment is terminated by heating (heat treatment), thereby inactivating the enzyme. Such heat treatment is not limited particularly as far as the enzyme can be inactivated, and for example, can be carried out by heating at a temperature around 60° C. for about 10 minutes.

The sample after the heat treatment may be subjected to condensing if desired. The condensing can be carried out by using commercially available equipment, for example, a centrifugal thickener (for example, 10000MWCO YM-10 of MILLIPORE CORPORATION).

The enzyme treatment can be carried out also by using an enzyme fixed to a solid phase (immobilized enzyme). A method of fixing the enzyme to a solid phase is known to a person ordinarily skilled in the art, and for example, β-galactosidase and/or sialidase can be fixed to agarose beads by using a coupling agent such as cyanogen bromide. Examples of such immobilized enzyme commercially available are immobilized β-galactosidase G3M (#A3102, MoBiTec), neuraminidase agarose derived from *Clostridium perfringens* (Welch *bacillus*) (Product No. N5254 available from SIGMA-ALDRICH), and the like. An advantage of use of an immobilized enzyme is such that an enzyme can be recovered without being inactivated by heat treatment after enzyme treatment, and as a result of such recovery, contaminants (proteins such as enzyme inactivated by heat treatment, and the like) can be decreased.

<Enzyme-Treated Bovine Colostrum>

The thus obtained enzyme-treated bovine colostrum of the present invention can be formed into a solid or a powder by freeze-drying. Such an enzyme-treated bovine colostrum is a novel composition which is useful for treatment, prevention, amelioration and maintenance of remission of diseases such as a cancer and an infectious disease.

<Pharmaceutical Composition, Pharmaceuticals>

The enzyme-treated bovine colostrum of the present invention can be used as a pharmaceutical composition as it is, or by optionally blending pharmaceutically acceptable auxiliaries (carriers) thereto. Any of auxiliaries used usually in this field can be used as such pharmaceutically acceptable auxiliaries, and examples thereof include a diluent, a stabilizer, a preservative, a buffer agent, an excipient, a binding agent, an antiseptic agent, a disintegrant, a lubricant, a flavoring substance and the like. These auxiliaries are blended optionally depending on a dosage form of the pharmaceutical composition.

The pharmaceutical composition of the present invention can be formed into pharmaceuticals by preparing into a proper dosage form. Such a dosage form is not limited particularly, and may be either of oral preparation or parenteral preparation. Examples of parenteral preparation include an injection agent, an infusion agent, nosal drops, ear drops, a suppository, an enteral nutrient, and the like. Examples of the injection agent include those administrated by intravenous injection, hypodermic injection, intradermal injection, intramuscular injection, intraperitoneal injection, and the like, and among these, intramuscular injection is preferred. Meanwhile, examples of the oral preparation include a powder, a granule, a tablet (including a sublingual tablet), a capsule, a pill, an enteric coating drug, a liquid for internal use (including a suspension agent, an emulsion, a syrup, and the like), an inhalant, and the like.

The dosage of the enzyme-treated bovine colostrum of the present invention varies depending on age, sex, body weight and symptom of a patient, an administration route, and the like. A representative example of the dosage for one dose is such that a total amount of proteins contained in the enzyme-treated bovine colostrum per 1 kg of body weight is not less than about 0.02 μg, preferably not less than about 0.2 μg, more preferably not less than about 2 μg, more preferably not less than about 20 μg, more preferably not less than about 200 μg, and not more than about 40 mg, preferably not more than about 20 mg, more preferably not more than about 13 mg, more preferably not more than about 10 mg, more preferably not more than about 2 mg. The preferred dosage is, for example, within a range of from about 0.02 μg to about 40 mg, preferably from about 0.02 μg to about 20 mg, more preferably from about 0.2 μg to about 20 mg, more preferably from about 2 μg to about 20 mg, more preferably from about 20 μg to about 20 mg, more preferably from about 200 μg to about 10 mg, more preferably from about 200 μg to about 2 mg. Other preferred dosage is within a range of from about 1 mg to about 40 mg, preferably from about 2 mg to about 20 mg, further preferably from about 3 mg to about 13 mg. Herein, the amount of protein is calculated from a protein concentration determined based on an absorbance at a wavelength of 570 nm.

With respect to the dosing interval and the number of doses, in case of dosing the pharmaceutical composition of the present invention with the above-mentioned dosage per one dose, the representative number of doses is 1 to 2 times per day. The dosage and the dosing interval may be optionally changed, using the total amount of proteins contained in the pharmaceutical composition as an index, as long as the total amount of proteins to be dosed is equal.

The pharmaceutical composition of the present invention has a macrophage activating action. Therefore, the pharmaceutical composition of the present invention can be used as a therapeutic agent or a prophylactic agent for diseases which can be cured or prevented by the action. Examples of such diseases are cancers and infectious diseases.

Cancers include any of carcinomas, sarcomas and malignant tumors, for example, carcinoma cutaneum, bronchial carcinoma, lung cancer, non-small-cell lung cancer, mammary cancer, ovarium cancer, tongue cancer, pharyngeal cancer, esophageal carcinoma, gastric cancer, intestinum tenue cancer, intestinum crassum cancer, rectum cancer, colon cancer, hepatic cancer, pancreas cancer, renal cancer, renal cell carcinoma, vesical cancer, prostatic cancer, uterine cancer, cervical cancer, Wilms' tumor, melanotic carcinoma, meningioma, neuroblastoma, osteosarcoma, Kaposi sarcoma, lymphoma, leukemia, and the like. In addition, herein, the term "cancer" includes these malignant tumors and metastases thereof.

Further, examples of infectious diseases are viral infectious diseases and bacterial infectious diseases, and for example, there are exemplified HIV infectious diseases, AIDS, and in addition, hepatitis b, hepatitis c, herpes, influenza, pneumonia, tuberculosis, EB virus infection, and the like.

The pharmaceutical composition of the present invention can be used in combination with other anticancer agents and anti-infectious agents. In the case of combination use, the dosage of the pharmaceutical composition of the present invention is properly adjusted in consideration of indication, effect and dosage of the other medicaments.

<Quasi Drug>

The enzyme-treated bovine colostrum of the present invention can be prepared not only as the pharmaceuticals as mentioned above but also as quasi drugs. To the quasi drug can be blended the above-mentioned auxiliaries and the like according to necessity. Further, the quasi drug can be formed into a solution, a suspension, a syrup, a granule, a cream, a paste, a jelly, and the like, and can be formed into a desired shape if necessary. The amount of the enzyme-treated bovine colostrum when used as a quasi drug is not limited particularly, and can be set optionally by referring to the dosage in the case of the above-mentioned pharmaceuticals.

<Composition for Food or Beverage, and Food or Beverage>

The enzyme-treated bovine colostrum of the present invention can be formed into a composition for food and beverage by optionally blending thereto the above-mentioned auxiliaries and various kinds of additives such as an edulcorant, a spice, a seasoning, an antiseptic agent, a preservative, a sanitizer, and an anti-oxidant which are usually used for a food or beverage, and also can be formed into a food or beverage comprising the composition for food or beverage by further processing the composition. The composition for food or beverage or the food or beverage can be formed into various shapes such as a solution, a suspension, a syrup, a granule, a cream, a paste, a jelly, and the like, and can be formed into a desired shape if necessary. Furthermore, the food or beverage can be formed into various shapes such as bread, noodle, confectionary, beverage, soup and fabricated food. Preparation of the composition for food or beverage and the food or beverage can be carried out by usual method.

The enzyme-treated bovine colostrum of the present invention shows its effect on the above-mentioned diseases, and therefore, the composition for food or beverage and the food or beverage of the present invention can exhibit effects thereof for prevention, amelioration and maintenance of remission of such diseases. In this case, the amount of enzyme-treated bovine colostrum in the composition for food or beverage or the food or beverage of the present invention is not limited particularly, and can be optionally set by referring to the dosage in the case of the above-mentioned pharmaceuticals. Preferred example of the amount of enzyme-treated bovine colostrum per a body weight of 1 kg is within a range of from about 1 mg to about 40 mg, preferably from about 2 mg to about 20 mg, further preferably from about 3 mg to about 13 mg for eating or drinking once.

The food or beverage of the present invention can be so-called health foods, health beverages, foods for specified health use, functional foods, nutritive supplements, and feeding stuff for animals other than a human being.

The pharmaceuticals, quasi drugs, and food or beverage of the present invention as mentioned above are preferably in such a form allowing the enzyme-treated bovine colostrum being an active ingredient to be absorbed via a digestive tract, preferably via an oral cavity or an intestine (for example, in a form of a sublingual tablet or an enteric coating drug as mentioned above). This is because an effect of directly activating macrophages in an oral cavity or an intestine can be expected. Especially it is known that an ample number of macrophages which are said to have the largest size in an internal body exist on a Payer's patch of a gut-associated lymphoid tissue (GALT).

EXAMPLE

The present invention is explained in detail by means of Examples, but is not limited to those examples.

1. Preparation of Enzyme-Treated Bovine Colostrum (1)

1 mg of solid bovine colostrum ("Colostrum Powder" of Now Foods) was dissolved in 1 ml of 1×PBS, and into 100 µl of the bovine colostrum solution were added 6.5 µl of β-galactosidase (10 MU/µl, Catalog No. 072-04141 available from Wako Pure Chemical Industries, Ltd.), 6.5 µl of sialidase (10 mU/µl, N2876 available from SIGMA-ALDRICH) and 87 µl of 100 mM SPB (15.601 g of $NaH_2PO_4 \cdot 2H_2O$ and 35.814 g of $Na_2HPO_4 \cdot 12H_2O$ were dissolved in 500 ml of distilled water to prepare 200 mM SPB (pH 7.0), followed by dilution into 100 mM SPB), followed by 3-hour incubation at 37° C. After the incubation, 200 µl of 100 mM SPB was further added thereto, followed by 10-minute heat treatment at 60° C. After the heat treatment, the solution was condensed with a MICROCON (10000MWCO YM-10, MILLIPORE CORPORATION), and a protein concentration was determined based on an absorbance at a wavelength of 570 nm (using a calibration curve made with respect to BSA (bovine serum albumin, SIGMA, A4503)). The protein concentration was 1.08 µg/µl (Sample 1).

Sample 1 was diluted using 100 mM SPB to prepare samples, each having protein concentrations of 1 ng/10 μl (Sample 1-1), 10 ng/10 μl (Sample 1-2), and 100 ng/10 μl (Sample 1-3), respectively.

Meanwhile, a protein concentration of the bovine colostrum before the enzyme treatment was determined in the same manner as above, and its protein concentration was 14.41 μg/μl (Comparative Sample 1). Comparative Sample 1 was diluted using 100 mM SPB to prepare samples, each having protein concentrations of 1 ng/10 μl (Comparative Sample 1-1), 10 ng/10 μl (Comparative Sample 1-2), and 100 ng/10 μl (Comparative Sample 1-3), respectively.

2. Phagocytotic Activity of Macrophage (1)

A mouse (8-week old, ICR female mouse, Japan SLC, Inc.) was made to suffer from cervical dislocation, an integument of its abdomen was peeled off, and 10 ml of phosphate buffered saline (PBS containing 0.01 M of sodium phosphate, 0.9% NaCl and 5 units/ml of heparin) was injected in its abdominal cavity without injuring viscera. After tapping of the abdomen for about one minute, an intra-abdominal liquid was recovered to collect peritoneal cells. After subjecting the recovered intra-abdominal liquid to centrifuging (1500 rpm, 4° C., 15 minutes), a supernatant was disposed, and an RPMI culture medium was added, followed by pipetting. The number of cells was measured with a Burker-Turk hemacytometer, and an RPMI culture medium was further added to adjust the number of cells to be $1.0 \times 10^6$ cells/ml. The RPMI culture medium was prepared in such a manner as mentioned below. Namely, after dissolving a powder culture medium (Catalogue No. 856846 available from GIBCO) in 900 ml of purified water, further, 2 g of $NaHCO_3$ was dissolved thereinto in a clean bench. After adjusting a pH value of the mixture to be 7.2 with 1N HCl, the total amount of the mixture was adjusted to be 1000 ml with purified water. The thus obtained solution was subjected to filtering with a filter (SLGVJ13SL of MILLIPORE) to obtain an RPMI culture medium which was then stored at 4° C. before the use.

The macrophage solution obtained above was dispensed in each of wells on a plate with 24 wells (TPP, 92024) in an amount of 500 μl/well ($5.0 \times 10^5$ cells/well), in which three sterilized cover glasses (Micro cover glass No. 1 of Matsunami Glass Ind., Ltd.) were put in each of wells. Further, an RPMI culture medium was added in an amount of 500 μl/well to be totally 1 ml/well. After subjecting the plate to 1-hour incubation at 37° C., the solutions in each of the wells were disposed, and each well was washed with 1 ml of RPMI culture medium twice. After the washing, 1 ml of an RPMI culture medium was added in each of wells, followed by 15-hour incubation at 37° C.

After the incubation, 10 μl each of Samples 1-1 to 1-3 and Comparative Samples 1-1 to 1-3 prepared above was added in each well, followed by 3-hour incubation at 37° C. to stimulate the macrophages. After the incubation, the solutions of each well were disposed, and 1 ml of 0.5% opsonized SRBC (sheep red blood cells of Nippon Bio-Supp. Center) was added, followed by 90-minute incubation at 37° C. to make the macrophages phagocytose the SRBC. After the phagocytosis, the cover glasses were washed with ⅕×PBS, 1×PBS and 1×PBS in order, followed by air drying for about 30 minutes. After the air drying, each cover glass was dipped in methanol (25183-2B of KANTO CHEMICAL CO., INC.) for about one minute to fix methanol to the cover glass. After the fixing, the cover glass was subjected to about 30-minute air drying again and then staining with a Giemsa solution (A1327 of SIGMA) diluted 20 times with PBS was conducted for one hour. After the staining, the cover glass was washed with tap water from its back surface and air-dried overnight.

After the air drying, the back surface of the cover glass was stuck to a slide glass (micro slide glass 52215 of Matsunami Glass Ind., Ltd.). Photographs were taken at 9 points per one cover glass with a light microscope (ECLIPSE E200 of Nikon Corporation). The number of macrophages, the number of phagocytosed SRBCs and the number of phagocytosing macrophages which were observed totally were counted and the respective total numbers at 9 points were summed up. An ingestion index was calculated by multiplying a ratio of macrophages having phagocytosed SBRC to the total macrophages counted by an average number of ingestions of one macrophage. For reference, FIG. 1 is a photograph after the Giemsa staining, which shows the states of "phagocytosing macrophages" and "phagocytosed SRBCs". By the Giemsa staining, macrophages are observed as purple spheres and SRBCs are observed as transparent spheres. The ingestion index was calculated based on the condition that SRBCs being in contact with macrophages were deemed as phagocytosed SRBCs and macrophages being in contact with SRBCs were deemed as phagocytosing macrophages.

For each of samples, two or three ingestion indices were calculated in the respective cover glasses, and an average thereof was obtained. With respect to a control, operations therefor were carried out in the same manner as above using RPMI culture media instead of the samples or comparative samples. The samples for which two ingestion indices were obtained were Comparative Samples 1-1 and 1-2, and for the remaining samples, three ingestion indices were obtained.

Figure 2:
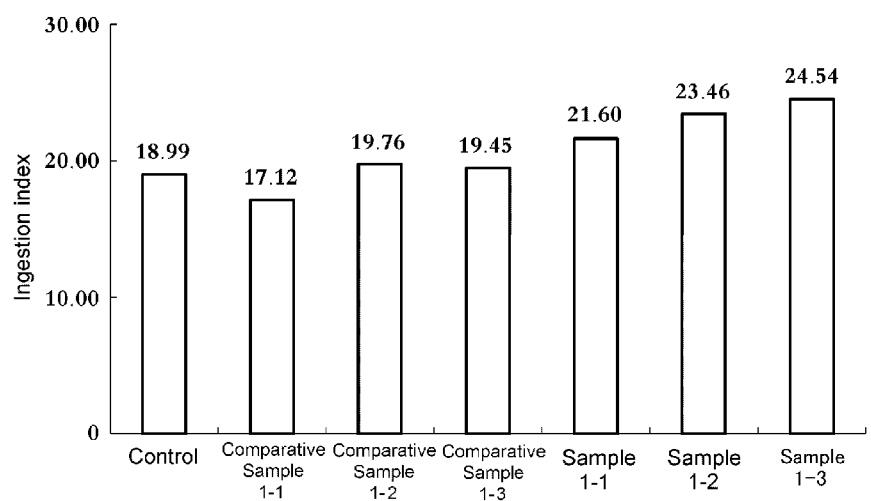
FIG. 2 is a graph showing the results of phagocytotic activity of macrophages by using 0.5% opsonized SRBC with respect to each of samples.

The results are shown in Table 1 (Phagocytotic activity of intra-abdominal mouse macrophage by using opsonized SRBC) and FIG. 2.

TABLE 1

|  | Amount of protein subjected to testing (ng) | Ingestion index (average value) |
| --- | --- | --- |
| Control | 0 | 18.99 |
| Comparative Sample 1-1 | 1 | 17.12 |
| Comparative Sample 1-2 | 10 | 17.96 |
| Comparative Sample 1-3 | 100 | 19.45 |
| Sample 1-1 | 1 | 21.60 |
| Sample 1-2 | 10 | 23.46 |
| Sample 1-3 | 100 | 24.54 |

3. Phagocytotic Activity of Intestinal Macrophages (Preparation of Each Sample)

An LPS sample was prepared by diluting LPS (Lipopolysaccharide, from *Escherichia coli*) (SIGMA, L2755) to 100 μg/ml with 100 mM PBS (pH=7.0). The LPS sample is one activating intestinal macrophages as described in the document (Seminars Immunopathology, 31(2), 178-84, 2009).

A blood serum sample was prepared by diluting un-treated human serum to 100 μg/ml with 100 mM PBS (pH=7.0).

An enzyme-treated human serum sample was prepared in accordance with the method of Patent Document 3 (WO 2013/038997) by diluting enzyme-treated human serum obtained by treating human serum in the same manner as in the above-mentioned method for the bovine colostrum to 100 μg/ml with 100 mM PBS (pH=7.0).

A bovine colostrum sample was prepared by diluting un-treated bovine colostrum to 100 μg/ml with 100 mM PBS (pH=7.0).

An enzyme-treated bovine colostrum sample was prepared by diluting an enzyme-treated bovine colostrum to 100 μg/ml with 100 mM PBS (pH=7.0).

(Preparation of Medium)

To 17 ml of an RPMI culture were dissolved 2 ml of collagenase D (Roche, 11088858001) and 1 ml of DNaseI (Roche 11284932001), followed by heating at 37° C. to prepare a collagenase medium.

(Measurement of Phagocytotic Activity)

In an abdominal cavity of a C57BL/6 female mouse (7-week old) was administrated 400 μl of chloral hydrate (Sigma, A2374) for anesthetization. A right abdomen of the mouse was dissected to expose the bowel, and after administration of each sample (1 mg/kg), the abdomen was closed. One hour after the administration, the abdomen was dissected again to expose the bowel, a non-tagged OVA protein (SIGMA, A5503-1G) and AF488 tagged OVA protein (Life Technologies, O34781) were administrated, and the abdomen was closed. One hour after the administration, the mouse was made to suffer from cervical dislocation, and the bowel was taken out. Fat and a Payer's patch were removed and cleaned with PBS while being careful in order not to injure the taken-out bowel. The bowel was cut into about 2 cm and was poured into 50 ml of an FACS buffer solution (prepared by adding 5 ml of FBS (inactivated) (available from GIBCO, 10437), 1 ml of EDTA (available from Nacalai Tesque, Inc., 15111-45, 500 mM), 1 ml of HEPES (available from MP, 1688449, 1M), 500 μl of sodium pyruvate (available from GIMCO, 11360-070, 100 mM), 20 μl of polymyxin B sulfate (available from GIMCO, 21850-029, 25 mg/ml) and 500 μl of penicillin/streptomycin (available from GIMCO, 15140-122, 10,000 U/ml) into 41.98 ml of phosphate buffered saline (PBS containing 0.01 M of sodium phosphate, 0.9% NaCl and 5 units/ml of heparin)) heated to 37° C., followed by 20-minute stirring (about 250 rpm) with a stirrer in an incubator at 37° C.

After the stirring, the bowel was taken out and washed three times with 30 ml of PBS. The bowel was placed on a dish of 10 cm diameter having a 10% FBS/RPMI culture. 4 ml of a collagenase medium was put in the dish, and the bowel was cut. In addition, 11 ml of a collagenase medium was put in the dish, and the dish was allowed to stand. Floating bubbles and fats were removed with an aspirator. The tissue in a vial was transferred into a flask. After the vial was washed with 5 ml of a collagenase medium, the washing liquid was put in the flask. The flask was put in a 37° C. incubator, and the content was subjected to one-hour stirring, After the stirring, 400 μl of 0.5 M EDTA (obtained from PBS having a pH of 8.0) was added thereto, followed by further 5-minute stirring. After the stirring, a supernatant was transferred to a tube capped with a cell strainer (FALCON, 352360). Meanwhile, 10 ml of the FACS buffer solution heated to 37° C. was added to the tissue, and was subjected to suspension. The whole suspension was passed through the cell strainer and debris remaining on the top of the strainer was squeezed out. The suspension was subjected to 10-minute centrifuging at 20° C. at 1,800 rpm. After the centrifuging, the supernatant was removed and the tissue was dispersed. The tissue was subjected to suspension with 10 ml of a 40% percoll, and the suspension was transferred to the tube and 5 ml of 75% percoll was put into the bottom of the tube with a capillary, followed by 20-minute centrifuging of the tube at 20° C. at 2,000 rpm. After the centrifuging, about 7 ml of the 40% percoll was removed with an aspirator from the top of the tube. After the removal, about 6 ml of the FACS buffer solution was added to the tube containing 5 ml of the FACS buffer solution, and further the 40% percoll was added thereto so that the total amount of the FACS buffer solution became 14 ml, followed by 10-minute centrifuging of the tube at 20° C. at 1,800 rpm. After the centrifuging, the supernatant was removed and 2 ml of the FACS buffer solution was put into the tube for suspension, and 1 ml of the solution was transferred to another tube, followed by 3-minute centrifuging of the tube at 20° C. at 1,500 rpm.

After the centrifuging, the supernatant was removed and 2 ml of the FACS buffer solution was added into the tube, and then Pacific® anti-mouse F4/80 antibody (Biolegend, 123124), PE/cy7 anti-mouse/human CD11b antibody (Biolegend, 101216) and CD16/32 anti-body (BD, 553141) were added thereto, followed by reaction at 4° C. Fifteen minutes after, the supernatant was removed and 2 ml of a wash buffer was added thereto, followed by 3-minute centrifuging at 20° C. at 1,500 rpm. After the centrifuging, 200 μl of a solution of 1 μg/ml 7-aminoactinomycin D (Sigma, A9400) was added thereto, and phagocytotic activity of intestinal macrophages was determined.

(Results)

The results are as shown in Table 2. In the enzyme-treated bovine colostrum, phagocytotic activity of ovalbumin (OVA) positive macrophage in an intestine was increased more as compared with an enzyme-treated blood serum.

TABLE 2

| Sample | LPS | Serum | Enzyme-treated blood serum | Bovine colostrum | Enzyme-treated bovine colostrum |
|---|---|---|---|---|---|
| Dosage (mg/kg) | 1 | 1 | 1 | 1 | 1 |
| OVA positive macrophage (%) | 26.9 | 2.6 | 7.2 | 4.5 | 25.5 |

4. Molecular Weight of Active Protein (HPA Positive) in Enzyme-Treated Bovine Colostrum and Enzyme-Treated Blood Serum (Preparation of Sample)

Novex (registered trademark) Sharp Pre-stained Protein Standard (Invitrogen®, 745065) was used as Marker 1.

An un-treated human blood serum diluted to 1 mg/ml with 100 mM PBS (pH=7.0) was used as a blood serum.

An enzyme-treated human blood serum obtained in the same manner as above was diluted to 1 mg/ml with 100 mM PBS (pH=7.0) and was used as an enzyme-treated blood serum.

WIDE-VIEW Prestained Protein Size Marker III (available from Wako, 230-02461) was used as Marker 2.

An un-treated bovine colostrum diluted to 1 mg/ml with 100 mM PBS (pH=7.0) was used as a bovine colostrum.

An enzyme-treated bovine colostrum diluted to 1 mg/ml with 100 mM PBS (pH=7.0) was used as an enzyme-treated bovine colostrum.

Each of the above samples was diluted to 1 μg/μl with distilled water, and 5 μl of each sample was mixed with 5 μl of a sample buffer (prepared by adding 50 μl of 2-mercaptoethanol (available from SIGMA, A2029) to 950 μl of Laemmli Sample Buffer (available from BIO-RAD, 161-0737), followed by 10-minute heat treatment at 100° C. to obtain a sample for electrophoresis.

An electrophoresis gel (XV PANTERA GEL, DRC, NXV-381D20) was set on an electrophoresis chamber (ERICA-MP, DRC, XVE-OMPC), and the electrophoresis chamber was filled with an electrophoresis buffer (prepared by dissolving a high speed SDS-PAGE electrophoresis buffer (available from DRC, NXV-BUFPTG) with 1,000 ml of distilled water). Each of the samples for electrophoresis was applied to each well of the set gels, followed by electrophoresis at 300 V. Amounts of samples applied for electrophoresis were 10 µl at a lane 1, 1 µl at lanes 2 and 3, and 5 µl at lanes 4, 5 and 6. After completion of the electrophoresis, the top portion of the gel was cut and disposed, and the gel was set on a transfer device (MINICA-MP, DRC, XVE-OMPB). A PVDF film (BIO-RAD, 162-0177) dipped for one minute in methanol (Kanto Chemical Industry Co., Ltd., 25183-2B) was placed on the gel, and transferring was carried out at 47 V for one hour.

After the transferring, the film was washed three times for 10 minutes with TBS-T (prepared by dissolving 8.0 g of NaCl, 0.2 g of KCL and 3.0 g of $H_2NC(CH_2OH)_3$ with 1,000 ml of distilled water to adjust a pH value to 7.4 and adding thereto 1 ml of polyoxyethylene (20) sorbitan monolaurate (available from Wako, 167-11515)). The film was dipped in a blocking solution (prepared by dissolving 100 mg of BSA (bovine serum albumin, SIGMA, A4503) with 10 ml of TBS-T), followed by one-hour shaking at room temperature. The film was washed three times for 10 minutes with TBS-T and dipped in a primary antibody HPA [prepared by diluting 10 µl of HPA Lectin (obtained by dissolving 1 mg of Lectin from *Helix Pomatia* biotin conjyugate, lyophilized powder, L6512 available from SIGMA with 1 ml of 100 mM SPB (pH=7.0)) with 10 ml of TBS-T], followed by one-hour shaking at room temperature. The film was washed three times for 10 minutes with TBS-T and was dipped in secondary antibody streptavidin (prepared by diluting 2 µl of streptavidin (available from GE Healthcare, RPN-1231) with 10 ml of TBS-T), followed by one-hour shaking at room temperature. The film was washed three times for 10 minutes with TBS-T.

Figure 3:
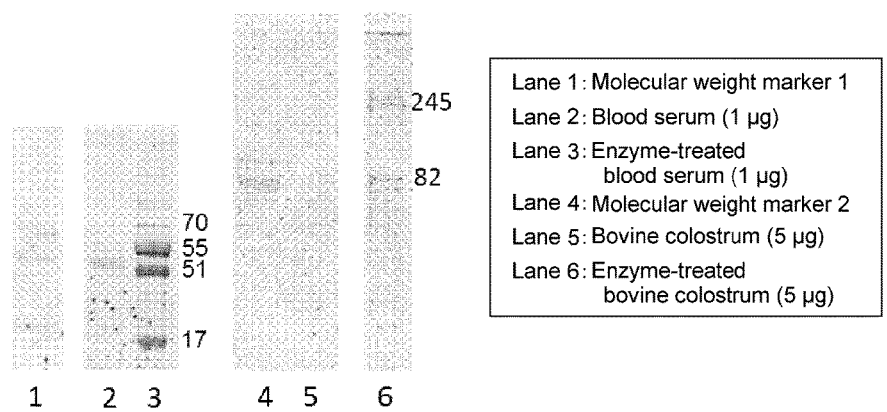
FIG. 3 is a photograph used in place of a drawing, which shows the results of electrophoresis.

The film was subjected to reaction with an ECL solution (prepared by adding 1 ml of a detection reagent 2 (ECL Western Blotting Detection Reagent, available from GE Healthcare, RPN2106V2) to 1 ml of a detection reagent 1 (ECL Western Blotting Detection Reagent, available from GE Healthcare, RPN2106V1)) for one minute in a plastic vessel, and pictures were taken by LumiCube (Liponics, Inc., 5003). After the pictures had been taken, the film was washed three times for 10 minutes with TBS-T and was dipped in a CBB dyeing liquid (PAGE Blue 83, COSMO BIO CO., LTD., 423406) for ten minutes, and bands of proteins were observed (FIG. 3). From the results of the observation, it was identified that the molecular weight of active protein (HPA positive) in the enzyme-treated bovine colostrum was 245, 82 kDa while the molecular weight of active protein (HPA positive) in the enzyme-treated blood serum was 70, 55, 51, 17 kDa.

5. Preparation of Enzyme-Treated Bovine Colostrum (2)

Each of samples having protein concentrations of 10 ng/10 µl (Sample 2-1) and 100 ng/10 µl (Sample 2-2), respectively was prepared by treating in the same manner as in the preparation of enzyme-treated bovine colostrum (1) except that sialidase was not used. A sample having LPS of 1 µg/10 µl was prepared as a positive control.

6. Phagocytotic Activity of Macrophages (2)

Ingestion indices were obtained in the same manner as in Phagocytotic activity of macrophages (1) using the above samples. The results are shown in Table 3 (Phagocytotic activity of intra-abdominal mouse macrophage by using opsonized SRBC).

TABLE 3

| | Amount of protein subjected to testing (ng) | Ingestion index (average value) |
|---|---|---|
| Control | 0 | 16.17 |
| Positive Control (LPS) | 1000 | 21.24 |
| Sample 2-1 | 10 | 26.52 |
| Sample 2-2 | 100 | 22.31 |

INDUSTRIAL APPLICABILITY

According to the present invention, it is possible to provide an enzyme-treated bovine colostrum which is useful for treatment, prevention, amelioration and maintenance of remission of diseases such as a cancer and an infectious disease, and a method of preparing the same.

EXPLANATION OF SYMBOLS

1 Phagocytosing macrophage
2 Phagocytosed SRBC
3 Macrophage

The invention claimed is:

1. An enzyme-treated bovine colostrum obtained by a method comprising
bringing a bovine colostrum into contact with β-galactosidase to produce an enzyme-treated bovine colostrum,
wherein one dose of said enzyme-treated bovine colostrum contains proteins in an amount of from 0.02 µg to 40 mg per 1 kg body weight of a patient, and
wherein said enzyme-treated bovine colostrum has macrophage activating action.

2. A pharmaceutical composition comprising the enzyme-treated bovine colostrum of claim 1.

3. The pharmaceutical composition of claim 2 wherein the pharmaceutical composition is suitable for treating a cancer or an infectious disease.

4. A composition for food or beverage, comprising the enzyme-treated bovine colostrum of claim 1.

5. A food or beverage comprising the composition for food or beverage of claim 4.

6. The enzyme-treated bovine colostrum claimed in claim 1, wherein the bovine colostrum is brought into contact with sialidase in addition to β-galactosidase.

7. A pharmaceutical composition comprising the enzyme-treated bovine colostrum of claim 6.

8. The pharmaceutical composition of claim 7, wherein the pharmaceutical composition is suitable for treating a cancer or an infectious disease.

9. A composition for food or beverage, comprising the enzyme-treated bovine colostrum of claim 6.

10. A food or beverage comprising the composition for food or beverage of claim 9.

11. The enzyme-treated bovine colostrum claimed in claim 1, wherein said method further comprises
heat treating after bringing the bovine colostrum into contact with β-galactosidase.

12. The enzyme-treated bovine colostrum claimed in claim 6, wherein said method further comprises
heat treating after bringing the bovine colostrum into contact with β-galactosidase and sialidase.

13. A single dosage form comprising 0.02 µg to 40 mg, per 1 kg body weight of a patient, of the enzyme-treated bovine colostrum of claim 1.

14. A single dosage form comprising 0.02 μg to 40 mg, per 1 kg body weight of a patient, of the enzyme-treated bovine colostrum of claim 6.

15. A method for treating a cancer or an infectious disease, comprising:
   administering the pharmaceutical composition of claim 3 to a patient in need thereof, wherein a single dose of the pharmaceutical composition contains 0.02 μg to 40 mg of the enzyme-treated bovine colostrum, per 1 kg body weight of the patient.

16. A method for treating a cancer or an infectious disease, comprising:
   administering the pharmaceutical composition of claim 8 to a patient in need thereof, wherein a single dose of the pharmaceutical composition contains 0.02 μg to 40 mg of the enzyme-treated bovine colostrum, per 1 kg body weight of the patient.

* * * * *